(12) United States Patent
Michaeli et al.

(10) Patent No.: US 9,860,520 B2
(45) Date of Patent: Jan. 2, 2018

(54) METHOD, SYSTEM, APPARATUS, AND COMPUTER PROGRAM FOR 3D ACQUISITION AND CARIES DETECTION

(71) Applicants: Daniel Michaeli, Riverdale, NY (US); Frank Thiel, Ober-Ramstadt (DE)

(72) Inventors: Daniel Michaeli, Riverdale, NY (US); Frank Thiel, Ober-Ramstadt (DE)

(73) Assignee: SIRONA DENTAL SYSTEMS GMBH, Bensheim (DE)

( * ) Notice: Subject to any disclaimer, the term of this patent is extended or adjusted under 35 U.S.C. 154(b) by 373 days.

(21) Appl. No.: 13/948,665

(22) Filed: Jul. 23, 2013

(65) Prior Publication Data

US 2015/0029309 A1 Jan. 29, 2015

(51) Int. Cl.
| | | |
|---|---|---|
| H04N 13/02 | (2006.01) | |
| H04N 9/47 | (2006.01) | |
| H04N 7/18 | (2006.01) | |
| A62B 1/04 | (2006.01) | |
| A61B 5/00 | (2006.01) | |
| G01B 11/245 | (2006.01) | |
| G01B 11/25 | (2006.01) | |

(Continued)

(52) U.S. Cl.
CPC ......... *H04N 13/0289* (2013.01); *A61B 1/247* (2013.01); *A61B 5/0068* (2013.01); *A61B 5/0071* (2013.01); *A61B 5/0088* (2013.01); *G01B 11/245* (2013.01); *G01B 11/25* (2013.01); *G02B 21/0028* (2013.01); *G02B 23/2407* (2013.01); *G02B 23/2415* (2013.01)

(58) Field of Classification Search
USPC .................................................. 386/223–224
See application file for complete search history.

(56) References Cited

U.S. PATENT DOCUMENTS

| | | | |
|---|---|---|---|
| 4,332,444 A * | 6/1982 | Nozawa ................... | G02B 7/10 396/14 |
| 4,575,805 A | 3/1986 | Moermann et al. | |

(Continued)

FOREIGN PATENT DOCUMENTS

| | | |
|---|---|---|
| DE | 10 2011 077 564 A1 | 12/2012 |
| EP | 0 968 687 A2 | 1/2000 |

(Continued)

OTHER PUBLICATIONS

3M ESPE, 3M True Definition Scanner brochure, copyright 2014, 4 sheets.

(Continued)

*Primary Examiner* — Hung Dang
(74) *Attorney, Agent, or Firm* — Fitzpatrick, Cella, Harper & Scinto

(57) ABSTRACT

A system and apparatus for obtaining images of an object, a method for operating an optical camera system to obtain images of the object, and a computer program that operates in accordance with the method. The system includes an optical system and at least one processing system. The optical system is arranged to capture at least one first image of the object while the optical system operates in an imaging mode, and is also arranged to capture at least one second image of the object while the optical system operates in a diagnostic mode. The at least one processing system is arranged to combine the first and second images.

14 Claims, 7 Drawing Sheets

(51) Int. Cl.
A61B 1/247 (2006.01)
G02B 21/00 (2006.01)
G02B 23/24 (2006.01)

(56) References Cited

U.S. PATENT DOCUMENTS

| | | | |
|---|---|---|---|
| 4,837,732 | A | 6/1989 | Brandestini et al. |
| 6,040,910 | A * | 3/2000 | Wu .................... G01B 11/2527 356/613 |
| 6,278,847 | B1 | 8/2001 | Gharib et al. |
| 6,697,164 | B1 | 2/2004 | Babayoff et al. |
| 6,813,035 | B2 | 11/2004 | Hoffmann |
| 6,885,464 | B1 | 4/2005 | Pfeiffer et al. |
| 7,355,721 | B2 | 4/2008 | Quadling et al. |
| 7,388,678 | B2 | 6/2008 | Forster et al. |
| 7,582,855 | B2 | 9/2009 | Pfeiffer |
| 8,237,835 | B1 * | 8/2012 | Muller ........................ 250/201.9 |
| 8,334,894 | B2 | 12/2012 | Pfeiffer et al. |
| 8,345,257 | B2 | 1/2013 | Bonnema et al. |
| 9,404,741 | B2 * | 8/2016 | Schick |
| 2005/0285038 | A1 * | 12/2005 | Frangioni ............ A61B 5/0059 250/330 |
| 2007/0207437 | A1 | 9/2007 | Sachdeva et al. |
| 2008/0063998 | A1 | 3/2008 | Liang et al. |
| 2010/0085636 | A1 | 4/2010 | Berner |
| 2011/0080576 | A1 | 4/2011 | Thiel et al. |
| 2012/0075425 | A1 | 3/2012 | Thiel |
| 2012/0122052 | A1 * | 5/2012 | Hackel ............... A61B 1/00096 433/29 |
| 2012/0282572 | A1 | 11/2012 | MacLeod et al. |
| 2012/0300895 | A1 | 11/2012 | Koivisto et al. |
| 2012/0322025 | A1 | 12/2012 | Ozawa et al. |
| 2013/0247398 | A1 * | 9/2013 | Durivault ................. G01B 3/40 33/199 R |
| 2013/0330684 | A1 * | 12/2013 | Dillon ................ A61B 1/00039 433/29 |
| 2014/0104406 | A1 | 4/2014 | Pfeiffer et al. |
| 2015/0148630 | A1 * | 5/2015 | Meester ............. A61B 1/00009 600/317 |
| 2015/0164335 | A1 * | 6/2015 | Van Der Poel ...... A61C 9/0053 433/29 |

FOREIGN PATENT DOCUMENTS

| | | |
|---|---|---|
| WO | 2011/095694 A1 | 8/2011 |
| WO | 2012/083967 A1 | 6/2012 |

OTHER PUBLICATIONS

3SHAPE, Trios Digital Impression Solution brochure, 2014, 28 sheets.
Kavo Dental GMBH, KaVo DIAGNOdent pen 2190—Display 2191 brochure, retrieved on Apr. 11, 2014, pp. 1-16.
E4D Technologies, NEVO brochure, retrieved on Apr. 11, 2014, 12 sheets.
Align Technology, Inc., iTero brochure, copyright 2013, 2 sheets.
Align Technology, Inc., "How It Works iTero: Intra Oral Digital Scanner," retrieved from http://www.itero.com/how-it-works, copyright 2013. pp. 1-11.
Sirona Dental Systems GMBH, "CEREC AC; Operating Instructions for the acquisition unit With Bluecam," Oct. 2012, pp. 1-66.
Sirona Dental Systems GMBH, "CEREC AC With CEREC Omnicam; Operating Instructions for the Acquisition Unit," Sep. 2013, pp. 1-76.
Sirona Dental Systems GMBH, CEREC Omnicam and CEREC Bluecam brochure, made available on Aug. 15, 2012 at http://www.sirona.com/en/products/digital-dentistiy/cerec-chairside-solutions/?tab=245 (follow "Brochures" hyperlink; then follow "CEREC Omnicam and CEREC Bluecam" hyperlink), 8 sheets.
Sopro, Soprolife Clinical Booklet, copyright 2013, pp. 1-42.
Lennon et al., "Residual caries detection using visible fluorescence," Caries Res., 2002, pp. 315-319, vol. 36.
International Search Report and Written Opinion of the International Searching Authority in PCT/EP2014/065779, dated Nov. 21, 2014.
H.J. Tiziani et al., "Three-Dimensional Analysis by a Microlens-Array Confocal Arrangement," Applied Optics, Feb. 1, 1994, pp. 567-572, vol. 33, No. 4.
J. Pfeiffer et al., "Dreidimensionale Optische Vermessung von Zähnen," Technisches Messen: Sensoren, Geräte' Systeme, Jun. 1996, pp. 254-261, vol. 63.
H.-J. Jordan et al., "Confocal White Light Microscopy," World Tribology Congress, Sep. 2001, pp. 1-4.
I. Pretty, "Caries Detection and Diagnosis: Novel Technologies," Journal of Dentistry, Nov. 2006, pp. 727-739, vol. 34.
J. Klim et al., "Innovation in Dentistry: CAD/CAM Restorative Procedures," ineedce.com, 2008, pp. 1-14.
Siemens AG, "Corporate Technology: Netzwerk der Kompetenzen— Partner für Innovationen", Nov. 28, 2008, p. 9, left column, with partial English translation.
P. Shirley et al., "Fundamentals of Computer Graphics," Fundamentals of Computer Graphics, Third Edition, 2009, pp. 243-259, A K Peters, Natick, Massachusetts.
J.S. Holtzman et al., "Ability of Optical Coherence Tomography to Detect Caries Beneath Commonly Used Dental Sealants," Lasers in Surgery and Medicine, 2010, pp. 752-759, vol. 42.
L. Karlsson, "Caries Detection Methods Based on Changes in Optical Properties Between Healthy and Carious Tissue," International Journal of Dentistry, 2010, pp. 1-9.
S. Chung et al., "Multispectral Near-IR Reflectance and Transillumination Imaging of Teeth," Biomedical Optics Express, Oct. 1, 2011, pp. 2804-2814, vol. 2, No. 10.
W. Lyda et al., "Advantages of Chromatic-Confocal Spectral Interferometry in Comparison to Chromatic Confocal Microscopy," Measurement Science and Technology, Mar. 22, 2012, pp. 1-7, vol. 23, No. 5.
Sirona Dental Systems GMBH, "Cerec SW Operator's Manual Software Version 4.0," Aug. 2012, pp. 1-82.
Stil S.A., "Optical Principles: 1 Confocal Chromatic," first accessed from http://www.stilsa.com/EN/pdf/optical%20principles%20CCS.pdf on Nov. 14, 2012, pp. 1-3.
Wikipedia, "3D Rendering," retrieved from http://en.wikipedia.org/wiki/3D_rendering, last updated on Sep. 26, 2013.
Wikipedia, "Correspondence Problem," retrieved from http://en.wikipedia.org/wiki/Correspondence_problem, last updated on Jun. 23, 2012.
M. Hillenbrand et al., "Parallelized Chromatic Confocal Systems Enable Efficient Spectral Information Coding," SPIE Newsroom, Jan. 17, 2013, pp. 1-3.
Wikipedia, "Depth of Field," retrieved from http://en.wikipedia.org/wiki/Depth_of_field, last updated on Sep. 25, 2013.

* cited by examiner

METHOD, SYSTEM, APPARATUS, AND COMPUTER PROGRAM FOR 3D ACQUISITION AND CARIES DETECTION

BACKGROUND

Field

Example aspects described herein relate generally to obtaining images in a dental environment, and, more particularly, to a method, system, apparatus, and computer program for 3D acquisition and caries detection.

Description of Related Art

In dentistry, diagnostic and treatment tasks utilize different devices. In treatment planning, 3-D cameras are often used to acquire 3-D contour data of a tooth and the surrounding dentition. The 3-D contour data is used in the preparation and placement of dental crowns, inlays, onlays, and other restorations. For diagnosis tasks, many optical technologies are used to detect the presence of dental decay. Existing devices and technologies used for treatment planning and diagnosis of dental decay are distinct and separate devices.

In the field of 3-D dental cameras, technologies known in the art include, for example, triangulation, color-coded pattern 3-D imaging, confocal imaging, and chromatic confocal imaging.

A 3-D camera is disclosed in the publication by J. Pfeiffer et al., entitled "Dreidimensionale Optische Vermessung von Zähnen", Technisches Messen: Sensoren, Geräte, Systeme [Metrology: Sensors, Devices, Systems], June 1996, pp. 254-261.

U.S. Pat. No. 6,885,464 describes a 3-D camera system which utilizes phase-shifting triangulation for determining height or depth differences of the surface structure of an object.

U.S. Pat. No. 6,813,035 describes a 3-D camera system which utilizes color-coding pattern technology to determine height or depth differences of the surface structure of an object.

U.S. Pat. No. 6,697,164 describes a 3-D camera system based on confocal imaging for determining height or depth differences of the surface structure of an object.

U.S. Patent Application Publication No. 2012/0075425 describes a chromatic confocal imaging technology for determining height or depth differences of the surface structure of an object.

Distinct from the 3-D imaging technologies, a variety of other optical technologies are commercially available to enable the diagnosis of dental decay. Examples of such diagnostic technologies include fiber-optic transillumination, quantitative light-induced fluorescence, and optical coherence tomography. Some of these are described in the journal article by I. Pretty, entitled "Caries Detection and Diagnosis: Novel Technologies", Journal of Dentistry, Volume 34, 2006, pp. 733-39.

SUMMARY

Existing limitations associated with the foregoing, as well as other limitations, can be overcome by a system and apparatus for obtaining images of an object, and by a method for operating an optical camera system, and a computer program that operates in accordance with the method.

According to an example embodiment herein, the system comprises an optical system and at least one processing system. The optical system is arranged to capture at least one first image of the object while the optical system operates in an imaging mode, and is further arranged to capture at least one second image of the object while the optical system operates in a diagnostic mode. In one example herein, the optical system is a self-contained camera. The at least one processing system is arranged to combine the first and second images.

In one example embodiment herein, the optical system operates in the imaging mode and the diagnostic mode simultaneously. In another example embodiment herein, the optical system operates in the imaging mode and the diagnostic mode non-simultaneously.

According to another example embodiment herein, the system is operable to select at least one of the imaging mode and the diagnostic mode.

Also in one example embodiment herein, the optical system further includes at least one optical source and an imaging sensor, wherein the at least one optical source is arranged to emit a light beam along a projection optical path to illuminate the object, and wherein the imaging sensor is arranged to receive light backscattered by at least one surface of the object, the backscattered light defining an observation optical path. The optical system, in still a further example embodiment herein, further includes a housing in which at least one of the at least one optical source and the image sensor are housed.

In some example embodiments herein, the optical system includes the projection optical path and the observation optical path, and at least one optic included in at least one of the paths, wherein the at least one optic includes at least one of an objective, a lens optic, an aperture array, interchangeable optics, and a prism. The interchangeable optics can include, for example, at least one of a confocal optic for the imaging mode and a fixed focus optic for the diagnostic mode. The confocal optic can be arranged to determine a height of the object within a predetermined range, and the fixed focus optic can be arranged to provide the optical system with a depth of field equal to the predetermined range.

In a further example embodiment herein, the optical system performs three-dimensional imaging by phase-shift triangulation while operating in the imaging mode, and performs transillumination imaging while operating in the diagnostic mode.

In another example embodiment herein, the optical system performs three-dimensional imaging by color-coded triangulation while operating in the imaging mode, and performs light-induced fluorescence imaging while operating in the diagnostic mode.

In another example embodiment herein, the optical system performs scanning confocal imaging while operating in the imaging mode, and performs light-induced fluorescence imaging while operating in the diagnostic mode.

In another example embodiment herein, the optical system performs chromatic confocal imaging while operating in the imaging mode, and performs light-induced fluorescence imaging while operating in the diagnostic mode.

In some example embodiments, the at least one first image is a three-dimensional image of the object and the at least one second image is a caries detection image.

The system can be useful for combining the distinct functionalities of three-dimensional imaging and optical dental diagnostic techniques to provide a combined dental treatment planning solution. Combining such distinct functionalities into a single system reduces equipment costs and inefficiencies compared to those associated with using separate equipment.

Further features and advantages, as well as the structure and operation of various embodiments herein, are described in detail below with reference to the accompanying drawings.

BRIEF DESCRIPTION OF THE DRAWINGS

The teachings claimed and/or described herein are further described in terms of exemplary embodiments. These exemplary embodiments are described in detail with reference to the drawings. These embodiments are non-limiting exemplary embodiments, in which like reference numerals represent similar structures throughout the several views of the drawings, and wherein:

FIGS. 4, 4A, and 4B are block diagrams of a camera constructed according to an example embodiment herein, to operate in either an imaging mode or a diagnostic mode, wherein FIG. 4 shows an embodiment of the camera having an interchangeable optic, FIG. 4A shows an embodiment of the camera where the interchangeable optic includes a confocal optic and the camera performs scanning confocal imaging while operating in the imaging mode, and FIG. 4B shows an embodiment of the camera where the interchangeable optic includes fixed focus optics arranged to provide a predetermined depth of field for the camera and the camera performs light-induced fluorescence imaging while operating in the diagnostic mode.

Figure 1:
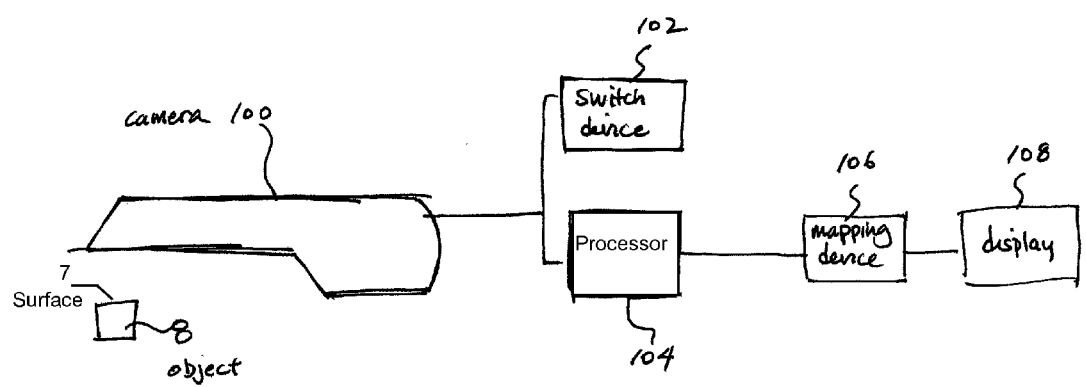
FIG. 1 is a system block diagram of a system according to one example embodiment herein.

Different ones of the Figures may have at least some reference numerals that are the same in order to identify the same components, although a detailed description of each such component may not be provided below with respect to each Figure.

DETAILED DESCRIPTION OF THE PREFERRED EMBODIMENTS

In accordance with example aspects described herein, a system as shown in FIG. 1 is provided for 3-D imaging and caries detection. The system comprises a camera 100 that can be operated, to obtain one or more images of an object 8 of interest, and also comprises devices 102-108. Camera 100 can be operated in at least one of a 3-D imaging mode and a caries detection mode. The camera 100 is electrically connected to switch device 102 and processor 104 (e.g., a microprocessor or controller). The switch device 102 has at least two settings, each corresponding to a respective one of the 3-D imaging mode and the caries detection mode, and configures the processor 104, such as to select one of those settings. Additionally, in one example aspect herein, the switch device 102 can configure (e.g., reposition) at least one element of the camera 100, such as, for example, one or more components of a lens system, an excitation laser, or other elements, depending on the particular embodiment employed. The switch device 102 can be controlled either manually or automatically.

When the switch device 102 is set to 3-D imaging mode, the camera 100 operates in 3-D imaging mode and the processor 104 can obtain a 3-D imaging data set representing for example, at least a surface 7 of object 8 in a manner to be described below. When the switch device 102 is set to caries detection mode the camera 100 operates in caries detection mode and the processor 104 can obtain caries detection data set representing a location of dental caries in object 8 in a manner to be described below.

Notably, the camera 100 can perform the 3-D imaging mode and the caries detection mode in a single self-contained device containing, for example, the optics for performing both modes, which simplifies registration and mapping of the caries detection data set on to the 3-D imaging data set. In one example embodiment herein, the 3-D imaging mode and caries detection mode acquire the 3-D imaging data set and the caries detection data set, respectively, of object 8 while the object 8 is in view of camera 100, and with a fast acquisition rate such that any spatial movement of the camera between the data sets has a negligible effect on the resulting data sets that are readily mapped. Of course, one or more images can be taken. In another example embodiment herein, any relative motion experienced by the camera 100 between the 3-D imaging mode and caries detection mode is detected by a motion detection device (not shown), such as an accelerometer, and the detected motion is compensated for to enable accurate registration and mapping of the data sets by mapping device 106. In one example embodiment, such detection and compensation are performed as described in U.S. Pat. No. 8,334,894, issued Dec. 18, 2012, entitled "Method and Device for Optical Scanning of Three-Dimensional Objects by Means of a Dental 3D Camera Using a Triangulation Method", by Pfeiffer et al. U.S. Pat. No. 8,334,894 is incorporated by reference herein in its entirety, as if set forth fully herein.

The processor 104 provides all data sets to mapping device 106. The mapping device 106, in one example embodiment herein, overlays the two-dimensional caries detection data set onto the 3-D imaging data set by employing one or more mapping methods. In one example embodiment, device 106 employs a mapping method such as that described in the publication by P. Shirley, entitled "Fundamentals of Computer Graphics", A K Peters/CRC Press, 2009, pp. 252-253, which is incorporated by reference herein in its entirety, as if set forth fully herein. According to this example embodiment, the mapping device 106 first associates the caries detection data set with a coordinate system, such as a (u,v), to create a texture map, and unwraps the 3-D imaging data set to create a two-dimensional polygon mesh having vertices, edges, and faces. The mapping device 106 then aligns the two-dimensional polygon mesh on the texture map and assigns (u,v) coordinates to vertices of the mesh. The two-dimensional polygon mesh with assigned (u,v) coordinates is then reassembled into a three-dimensional model, and a diagnostic rendering is created by overlaying pixels of the texture map on the three-dimensional model based on the (u,v) coordinates assigned to the vertices of the model. Of course, other types of mapping can be employed instead.

The diagnostic rendering is displayed to the user on display 108. In some embodiments herein, one or more of devices 102-108 can be included as part of camera 100, although they are shown separately in the illustrated example embodiment. Also, in some example embodiments, one or more the devices 102-108 can be included in a single processing system (e.g., a microprocessor), although they are shown separately in the illustrated example embodiment.

Figure 2:
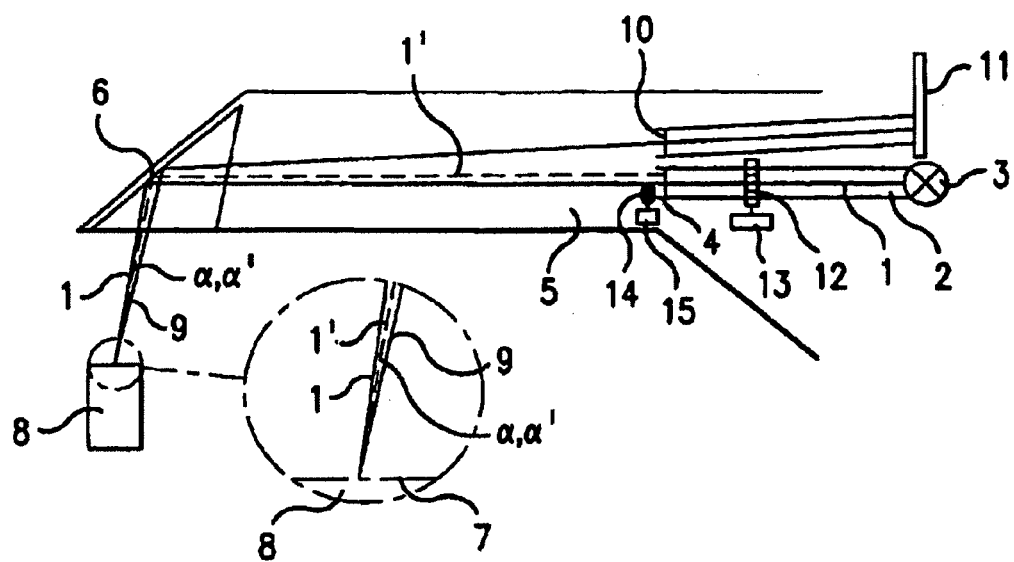
FIG. 2 is a block diagram of a camera constructed according to an example embodiment herein, to perform three-dimensional imaging by phase-shift triangulation while operating in an imaging mode, and to perform transillumination imaging while operating in a diagnostic mode.

Reference will now be made to FIG. 2 which, in one example embodiment herein, shows a 3-D imaging and caries detection camera 200 used in conjunction with an object 8 of interest (e.g., one or more teeth) being imaged. The camera 200 can be a more detailed representative example of the camera 100 of FIG. 1. According to the example embodiment illustrated in FIG. 2, the 3-D imaging mode is provided by means of phase-shift triangulation and the caries detection mode is provided by means of a transillumination technique, operating in a backscatter configuration.

Examples of phase-shift triangulation are described in a publication by J. Pfeiffer et al., entitled "Dreidimensionale Optische Vermessung von Zähnen", Technisches Messen: Sensoren, Geräte, Systeme [Metrology: Sensors, Devices, Systems], June 1996, pp. 254-26; U.S. Pat. No. 6,885,464, issued Apr. 26, 2005, entitled "3-D camera for Recording Surface Structures, in Particular for Dental Purposes", by Pfeiffer et al.; and U.S. Pat. No. 4,575,805, issued Mar. 11, 1986, entitled "Method and Apparatus for the Fabrication of Custom-Shaped Implants", by Moermann et al., which are incorporated by reference herein in their entireties, as if set forth fully herein.

Referring to FIG. 2, a projection optical path 1 is defined by a group of light beams 2 which can be produced by an optical source 3. For example, the optical source 3 can include an LED (or other light source). The projection optical path 1 is represented by a centroid beam, which, in one example embodiment, is a beam that forms an average in relation to the cross sectional area and intensity of the group of light beams 2. More precisely, the position of the centroid beam in a cross-sectional plane of the group of light beams is obtained by averaging the cross-sectional point coordinates weighted with the respective light intensity. In a group of light beams with uniform intensity and circular form, the centroid beam passes through the center of the circle.

The group of light beams 2 of the projection optical path 1 passes through a diaphragm 4 into a prism tube 5 from which the group of light beams then emerges towards object 8, after deviation by means of a prism 6, at a predetermined angle with respect to a longitudinal axis of the prism tube 5. The group of light beams emerging from the prism tube 5 via the prism 6, represented by the centroid beam, strikes at least one surface 7 of an object 8 (e.g., a patient's tooth) to be measured and is backscattered there.

The backscattered group of light beams 2 passes along an observation optical path 9. The centroid beam of the observation optical path 9 intersects the surface 7, and an angle $\alpha$ referred to as the triangulation angle is included between the projection optical path 1 and the observation optical path 9. The light backscattered by the object 8 of interest is again deviated along the observation optical path 9 via the prism 6 and is delivered through the prism tube 5 and a second diaphragm 10 to an image sensor 11, (e.g. a charge-coupled device (CCD), a complementary metal-oxide-semiconductor (CMOS) sensor, or the like). The image sensor 11 includes, for example, an array of pixel sensors. In one example embodiment, the image sensor 11 is disposed within camera 200. In another example embodiment, the image sensor 11 and/or optical source 3 are disposed in a unit external to the camera 200, and the unit and camera 200 are optically connected by a light guide (not shown). The image sensor 11 converts the received light signals into a two-dimensional image of the object 8, which is then delivered to a processor (such as device 104 of FIG. 1).

During the 3-D imaging mode, a grating 12 can be inserted into the projection optical path 1 for phase-shift triangulation. The grating 12 can be inserted as described above either manually by the operator, in one example, or in another example, by way of control by processor 104 under control of switch device 102. Alternatively, instead of a mechanical grating, an LCD element can be employed for generating a reference pattern.

The grating 12 can be moved in a direction perpendicular to the lines of the grating by a piezo actuator 13. The grating 12 is arranged in the beam in such a way that an image of the grating is projected onto the surface 7, forming a reference pattern, such as a parallel stripe pattern, on the surface 7. By activating the piezo actuator 13, the grating 12 is moved cyclically in a direction perpendicular to the grating lines, in one non-limiting example, and the reference pattern correspondingly moves, for example, cyclically across the surface 7. Periodically during a cycle of grating movement, image sensor 11 acquires, for example, four successive images of the reference pattern on surface 7. Because in one example the four images are acquired over one cycle of movement, the images correspond to phase shifts of, for example, 0°, 90°, 180°, and 270° of the reference pattern on the surface 7. These two-dimensional images are then used by processor 104 to calculate information about the third-dimension of the object, i.e., the height the surface 7. In one example, this is done by first taking the differences between the image for the 0° phase shift and the image for the 180° phase shift to create the 0°-180° image. Similarly, the difference between the 90° and 270° images creates the 90°-270° image. The values stored at corresponding pixels of the 0°-180° image and the 90°-270° image can be shown to correspond to the real and imaginary parts, respectively, of a complex number. The phase angle of this complex number is then proportional to the height of surface 7 of the corresponding pixel, and a phase angle image can be created by calculating this phase angle for each corresponding pixel. A 3-D imaging data set is created from at least one phase angle image.

During caries detection mode, the grating 12 need not be present in the projection optical path 1. According to one example embodiment herein, the grating 12 is not included in the projection optical path 1 or can be controllably removed therefrom. Alternatively, according to another example embodiment, the light beams 2 are diverted around the grating 12 by an arrangement of mirrors or prisms (not shown) inserted in the projection optical path 1, but otherwise follow the same path as shown in FIG. 2. The grating 12 can be removed from the projection optical path 1 and the arrangement of mirrors or prisms can be inserted into the projection optical path 1, either manually by the operator, in one example, or in another example, by way of control by processor 104 under control of switch device 102.

In one example embodiment herein, the diaphragm 4 can be shaded or shadowed in a lower region for use during the 3-D imaging mode so as to shift the centroid beam upwards in the projection optical path 1, as represented by the dashed line 1'. Consequently, the observation optical path is also shifted (not shown). By virtue of the projection optical path 1' with a partially shaded diaphragm 4, the triangulation angle $\alpha$ is reduced, as represented by angle $\alpha'$. Altering the triangulation angle to bring about an alteration to the centroid beam of the projection and/or observation optical path advantageously permits unambiguous measurements to be obtained when there are large height differences in object 8 while maintaining a compact structure of camera 100. During caries detection mode, in one example, the diaphragm 4 is fully opened such that no part of the group of light beams 2 is shaded or shadowed.

When the switch device 102 is set to caries detection mode, the camera 100 and processor 104 are configured to perform transillumination caries detection. The optical source 3 is configured, in one example aspect, to have increased intensity relative to the intensity utilized during the 3-D imaging mode. The optical source 3 also may have a capability to output a wavelength particularly advantageous for transillumination caries detection, such as wavelengths from about 1300 nm to about 1460 nm, although these examples are non-limiting. The image sensor 11, in one example, can have a high dynamic range. For example, to increase the dynamic range of the image sensor 11, the integration time of a photodetector-based image sensor 11 is increased relative to the integration time utilized during the 3-D imaging mode. Also, the image sensor 11 can have a high full well capacity such that only a portion of the dynamic range is utilized by the 3-D imaging mode but excess dynamic range is available for the caries detection mode. The processor 104 analyzes the image obtained from the image sensor 11 so as to create a caries detection data set. In one example embodiment herein, the caries detection data set includes grey scale images of the patient's teeth useful for detecting and diagnosing dental caries. For example, dental caries can appear as white spots on the grey scale images due to increased light scattering within demineralized, caries-affected portions of the tooth structure.

Other optical elements besides those depicted in the mentioned figures can also be employed, although they have not been represented for the sake of simplicity. Examples of various optical elements that can be employed are described in the aforementioned publication by Pfeiffer, J., et al entitled "Dreidimensionale Optische Vermessung von Zähnen," on page 257 and FIG. 6, and aforementioned U.S. Pat. No. 6,885,464, as well as aforementioned U.S. Pat. No. 4,575,805.

As can be appreciated in view of the description of the present embodiment, both the 3-D imaging mode and the caries detection mode can be carried out using the same single camera 200. As a result, the 3-D imaging data set and the caries detection data set can be readily combined by the mapping device 106 and presented to the user as a diagnostic rendering on display 108 as described above.

Figure 3:
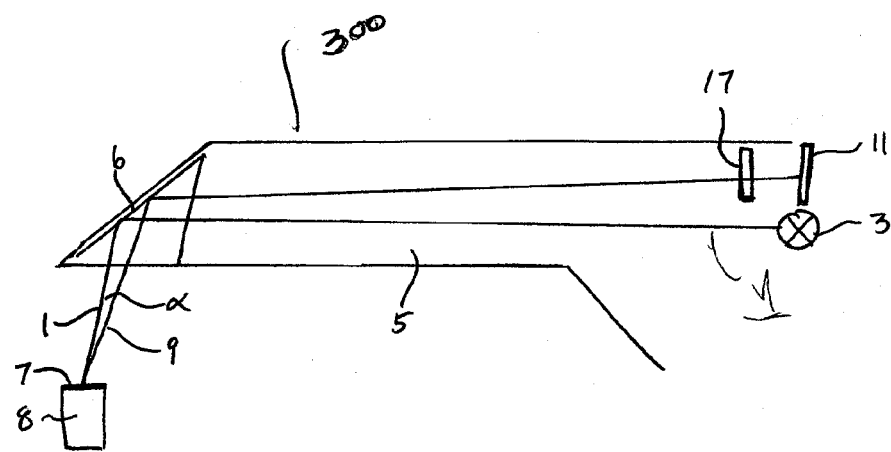
FIG. 3 is a block diagram of a camera constructed according to an example embodiment herein, to perform three-dimensional imaging by color-coded triangulation while operating in an imaging mode, and to perform light-induced fluorescence imaging operating in a diagnostic mode.

According to another example embodiment, illustrated in FIG. 3, the 3-D imaging mode is provided by means of color-coded 3-D triangulation and the caries detection mode is provided by means of a quantitative light-induced fluorescence technique.

Referring now to FIG. 3, a camera 300 is shown along with object 8. The camera 300 can form camera 100 of FIG. 1, in one example embodiment. A projection optical path 1 represents the projection of color pattern-encoded light which can be produced by optical source 3. In one example embodiment herein, the optical source 3 can include LEDs of at least three colors, such as, for example, red, green, and blue. By combining LEDs of three colors, it is possible, for example, to produce for projection optical path 1 a light beam of at least eight colors, including black, blue, green, cyan, red, magenta, yellow, and white, and to project a color pattern having identifiable landmarks onto surface 7 of object 8 for robust triangulation, as described in U.S. Pat. No. 6,813,035, issued Nov. 2, 2004, entitled "Method for Determining Three-Dimensional Surface Coordinates", by Hoffmann, and U.S. Pat. No. 7,388,678, issued Jun. 17, 2008, entitled "Method and Device for Three-Dimensionally Detecting Objects and the Use of This Device and Method", by Forster et al., which are incorporated by reference herein in their entireties, as if set forth fully herein. In another example embodiment herein, the optical source 3 may produce a single color only, such as, for example, blue. A blue LED may be employed as optical source 3 having the blue color, or, in another example embodiment herein, the optical source 3 may be a multiple color optical source that produces light of the single color in the projection optical path 1 and which light has a wavelength of 370 nm.

The color pattern-encoded light provided by optical source 3 follows a projection optical path 1 and is backscattered from the surface 7 of object 8 along observation optical path 9 to image sensor 11 in a manner substantially similar to that described above with respect to FIGS. 1 and 2. Triangulation angle α is formed between the projection optical path 1 and observation optical path 9. Similar to the embodiment described above, the image sensor 11 and/or optical source 3 may be disposed within camera 300 in one example or, in another example, may be disposed in a unit external to camera 300, the unit being connected to the camera by a light guide (not shown).

Referring to FIG. 3 in conjunction with FIG. 1, the image sensor 11 converts the received light signals into two-dimensional images which are then delivered to the processor 104 (FIG. 1). In one example embodiment herein, the image sensor 11 may be a solid state imaging device, such as, for example, a CCD or CMOS sensor, having an array of pixel sensors, each pixel sensor being sensitive to either red, green, or blue light. An optical filter 17, such as, for example, a long pass filter, which attenuates wavelengths of about 370 nm and transmits wavelengths greater than 540 nm, may be interposed in the observation optical path 9.

When the switch device 102 (FIG. 1) is set to 3-D imaging mode, the optical filter 17 is removed from the observation optical path 9. This can be done either manually by the operator, in one example, or in another example, by control of processor 104 under control of switch device 102. The processor 104 analyzes the two-dimensional images provided by image sensor 11 to calculate information about the third-dimension of the object 8, i.e. height of the surface 7 and obtain a height image (e.g., a 3-D image), in a known manner as described above. A 3-D imaging data set can be created from one or more height image.

When the switch device 17 is set to caries detection mode, the switch device 102 configures, as described below, at least one of the optical source 3, optical filter 17, image sensor 11, and processor 104. In one example embodiment, the optical source 3 emits blue light of a wavelength of about, for example, 370 nm, for the purpose of providing excitation light to induce fluorescence in dental enamel, although this example is not limiting.

For caries detection mode, blue excitation light may be removed from the observation optical path 9 by optical filter 17 such that the image sensor 11 detects primarily the fluorescence light emitted from the dental enamel. In one example embodiment herein, the optical filter 17 is inserted into the observation optical path 9, either manually by the operator, in one example, or, in another example, by way of processor 104 under control of switch device 102. Alternatively, an arrangement of mirrors or prisms (not shown) may be inserted into the observation optical path 9 to divert the observation optical path 9 through the optical filter 17. In one example embodiment herein, the image sensor 11 may be sensitive only to wavelengths greater than 540 nm, for example, so that it outputs only data from the red and green pixel sensors of image sensor 11 to the processor 104, whether or not optical filter 17 is employed in camera 300. The processor 104 analyzes the two-dimensional images provided by the image sensor 11 so as to obtain a caries detection data set in a similar manner as described above.

In one example embodiment herein, differences in intensities of the fluorescence light detected from the dental enamel can be indicative of dental caries, and can enable detection and diagnosis of dental caries. For example, when subjected to excitation light having a wavelength of 370 nm, carious dental enamel fluoresces at a reduced intensity compared to healthy dental enamel because demineralized carious dental enamel increases scattering of excitation and fluorescence light. Thus, areas of reduced fluorescence intensity can indicate the presence of dental caries.

Notably, in the embodiment of FIG. 3, the optical source 3 and image sensor 11, useful for both 3-D imaging by color pattern-encoded triangulation and caries detection by quantitative light-induced fluorescence, are included within the same camera 300. As a result, the 3-D imaging data set and the caries detection data set can be readily combined by the mapping device 106 and presented to the user as a diagnostic rendering on display 108 as described above.

Figure 4:
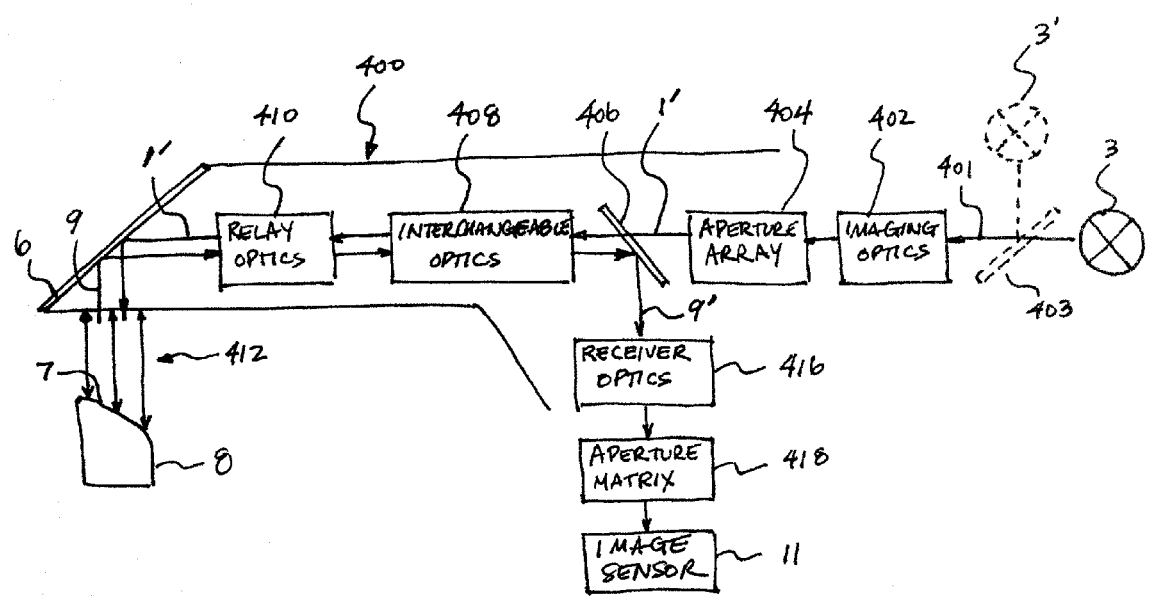

According to another example embodiment, illustrated in FIG. 4, the 3-D imaging mode is provided by means of parallel confocal imaging and the caries detection mode is provided by means of a quantitative light-induced fluorescence technique. In FIG. 4, a camera 400 is shown along with object 8. The camera 400 can form camera 100 of FIG. 1, in one example embodiment.

Examples of parallel confocal systems are described in U.S. Pat. No. 7,582,855, issued Sep. 1, 2009, entitled "High-Speed Measuring Device and Method Based on a Confocal Microscopy Principle", by Pfeiffer, and U.S. Pat. No. 6,697,164, issued Feb. 24, 2004, entitled "Imaging a Three-Dimensional Structure by Confocal Focussing an Array of Light Beams", by Babayoff et al., which are incorporated by reference herein in their entirety, as if set forth fully herein.

Referring to FIG. 4, optical source 3 produces a light beam in light path 401. In one example embodiment, the optical source can emit monochromatic light. In another example embodiment herein, the optical source can emit white light. For example, white light may include, in part, a wavelength of about 370 nm. In another embodiment wherein the optical source 3 does not emit light including a wavelength of 370 nm, during caries detection mode, the optical source 3 may optionally be disabled and a second optical source 3' is provided to emit light including a wavelength of about 370 nm, either manually by the operator, in one example, or in another example, by way of processor 104 under control of switch device 102. Light emitted by the second optical source 3' is directed into the path 401 by a diverting mechanism 403 such as, for example, a beamsplitter 403

In either case, the beam propagated in path 401 passes through imaging optics 402 and then aperture array 404 to form an array of light beams 412, represented by projection optical path 1'. The imaging optics 402 may be, for example, a beam expander which expands the beam to more fully illuminate the aperture array 404. The aperture array 404 may be, for example, a grating, a drilled board, or a microlens array. Transforming the beam propagated in path 401 into an array of light beams 412 propagated along path 1' provides a mechanism to obtain a planar image without scanning the camera, for example, by raster scanning.

Figure 4A:
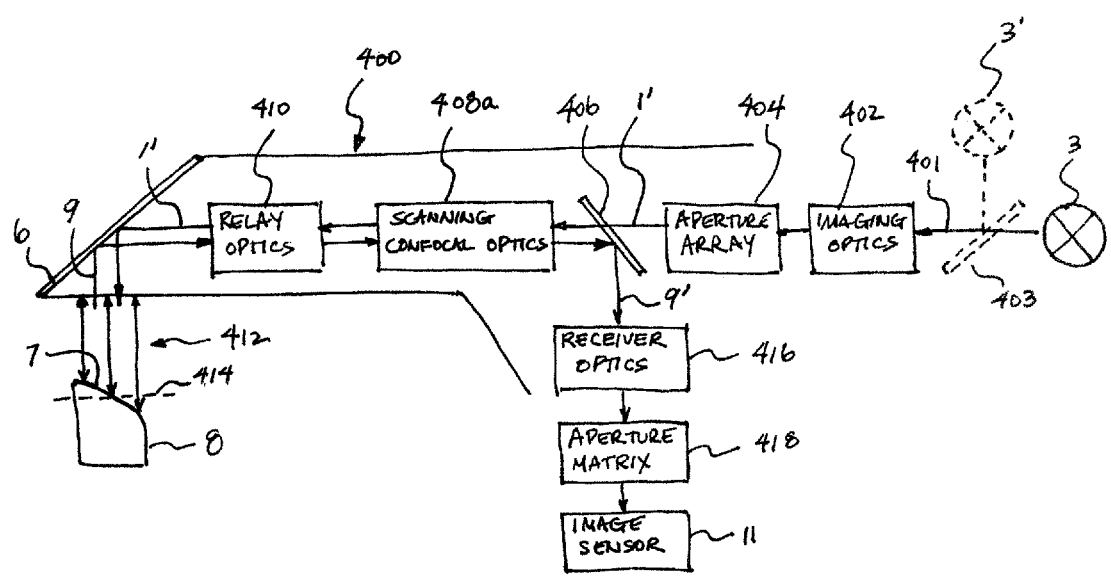
Figure 4B:
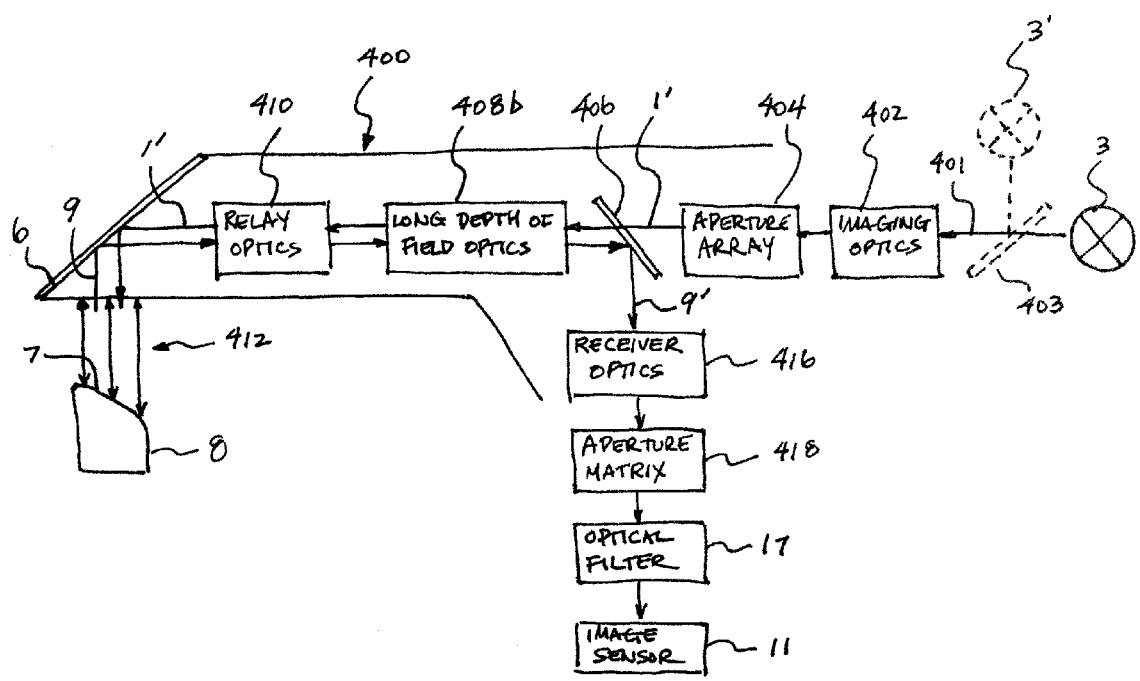

The light beam array 412 propagates along 1' and passes through a deflecting mechanism 406, such as, for example, a beamsplitter or a partially transparent mirror, which transmits light received thereby along projection optical path 1' but which reflects light traveling in the opposite direction. The light beam array 412 then continues along projection optical path 1' through interchangeable optics 408, is transmitted down the length of the camera by relay optics 410, is directed out of the camera 400 by prism 6, impinges on the surface 7 of object 8, and backscatters from there. The interchangeable optics 408 can include optics enabling the 3-D imaging mode (for example, scanning confocal optics 408a as represented in FIG. 4a), and/or optics enabling the caries detection mode (for example, long depth of field optics 408b as represented in FIG. 4b). Which type of optics is employed for optics 408 can be selected in one example embodiment herein, by repositioning the scanning confocal optics (e.g., 408a) into the light path and repositioning the long depth of field optics (e.g., 408b) out of the light path, or vice versa, or, in another example embodiment, by inserting an arrangement of mirrors or prisms (not shown) to divert the light path through either the scanning confocal optics (e.g., 408a) or the long depth of field optics (e.g., 408b). In the aforementioned example embodiments, repositioning of the interchangeable optics 408 and the inserting of an arrangement of mirrors or prisms may be performed either manually by the operator, in one example, or in another example, by way of processor 104 under control of switch device 102.

Referring again to the backscattered light, the backscattered light returns through the camera 400 along observation optical path 9 and is again deviated by prism 6 to pass through relay optics 410 and interchangeable optics 408 towards deflecting mechanism 406. The backscattered light is deviated by deflecting mechanism 406 along path 9' and through receiver optics 416 and aperture matrix 418 to image sensor 11. In one example embodiment, the receiver optics 416 include, for example, a lens or a plurality of lenses that transform the backscattered light in a manner such that the cross-sectional plane of the backscattered light fully illuminates and coincides with the aperture matrix 418. In one example embodiment, the aperture matrix 418 may be an array of pinholes. The image sensor 11 having an array of pixel sensors, such as, for example, a CCD or CMOS sensor, converts the received array of light beams into a two-dimensional image which is then delivered to a processor 104. In one example embodiment, each aperture of the aperture matrix 418 corresponds to one pixel of the image sensor 11 of FIG. 1.

Similar to the embodiment described above, the image sensor 11 and/or optical source 3 may be disposed within camera 400 in one example or, in another example, may be disposed in a unit external to camera 400, the unit being connected to the camera by a light guide (not shown). FIG. 4a illustrates the embodiment of FIG. 4 when the switch device 102 is set to 3-D imaging mode. As described above, in 3-D imaging mode, the interchangeable optics 408 of FIG. 4 are scanning confocal optics 408a of FIG. 4a. The scanning confocal optics 408a defines a focal plane 414 (FIG. 4a), by focusing each beam of the array of light beams 412 to the same focal length, and translates the focal plane 414 disposed along a Z-axis over a scanning range, the Z-axis being defined as part of the projection optical path provided between camera 400 and object 8. The scanning confocal optics 408a may be, by example only, moveable telecentric confocal optics linked to a motor. Examples of various types of optical elements that can be employed for optics 408a are described in the aforementioned U.S. Pat. No. 7,582,855, as well as U.S. Patent Application Publication No. 2010/0085636, published on Apr. 8, 2010, entitled "Optical System for a Confocal Microscope", by Berner, which is incorporated by reference herein in its entirety, as if set forth fully herein.

During 3-D imaging mode, an array of light beams 412 from projection optical path 1' strikes surface 7 of object 8, which surface 7 may or may not be even. The beams 412 striking the surface 7 of object 8 at the focal plane 414 are in focus while beams striking the surface 7 at other locations outside of the focal plane are out-of-focus. Backscattered in-focus beams will (after propagating by way of devices 6, 410, 408a, and 416) also be in focus at the aperture matrix 418 and pass through to the image sensor 11. Backscattered light arriving from out-of-focus beams will (after propagating by way of devices 6, 410, 408a, and 416) be attenuated by aperture matrix 418, resulting in lower detected intensity than that of in-focus beams at the image sensor 11. As a result, in-focus beams have a relatively greater intensity at the image sensor 11 than the attenuated out-of-focus beams, and the shape of a surface 7 of object 8 in any given focal plane 414 can be determined from the in-focus light beams detected by the image sensor 11. As the scanning confocal optics 408a scans through the scanning range by translating the focal plane 414, the processor 104 of FIG. 1 compiles two-dimensional images provided by the image sensor 11 from each focal plane in the scanned range. The processor 104 creates a height image by analyzing the compiled two-dimensional images to find the image with the highest intensity at each pixel location, and storing the corresponding Z-axis location of that highest intensity image at a corresponding pixel location of the height image. A 3-D imaging data set is created from at least one height image.

FIG. 4b illustrates the embodiment of FIG. 4 when the switch device 102 is set to caries detection mode. As described above, in caries detection mode, the interchangeable optics 408 of FIG. 4 may be long depth of field optics 408b of FIG. 4b. The long depth of field optics 408b operates in a complementary fashion with other optics in projection optical paths 1 and 1', and observation optical paths 9 and 9', such that camera 100 has, for example, a fixed focal length and a depth of field equal to or greater than the scanning range of the camera 100 operating in the 3-D imaging mode with scanning confocal optics 408a. Thus, the long depth of field optics 408b itself need not have an actual long depth of field characteristic (although in some embodiments it may have such a characteristic), so long as, by virtue of its interaction with other optics in camera 100, the camera 100 has a fixed focal length and depth of field as described above. The long depth of field optics 408b can also have, for example, wavelength-dependent transmission properties, and, more particularly, a high transmittance for wavelengths between about 370 nm to about 800 nm. In one example embodiment herein, the long depth of field optics 408b include the telecentric confocal optics from scanning confocal optics 408a and a small-diameter aperture in the observation optical path 9, although the scope of the invention is not limited to that example only. Because the depth of field is a function of the ratio of the focal length to the aperture diameter, the aperture diameter can be selected to provide a depth of field equal to or greater than the scanning range of the scanning confocal optics. The extent to which the aperture diameter may be reduced in order to obtain a longer depth of field for camera 100 is practically limited by other consequences of reducing aperture diameter, such as the decrease in the amount of light transmitted through to image sensor 11 and an increase in diffraction.

In caries detection mode, the surface 7 of object 8 can include, for example, dental enamel. In one example embodiment herein, the optical source 3 emits, at least in part, blue light, for example, having a wavelength of about 370 nm. Blue light striking the surface 7 of object 8 may cause dental enamel included in object 8 to emit fluorescence light having a wavelength of about 540 nm or greater. The fluorescence light together with light from optical source 3 backscattered from object 8 enters the camera 400 along observation optical path 9.

In caries detection mode, blue light may be removed from the observation optical path 9' such that the image sensor 11 detects primarily the fluorescence light emitted from the dental enamel. An optical filter 17, such as, for example, a long pass filter, which attenuates wavelengths of about 370 nm and transmits wavelengths greater than 540 nm, may be interposed in the observation optical path 9' before the image sensor 11, either manually by the operator, in one example, or in another example, by way of processor 104 under control of switch device 102. In one example embodiment, an arrangement of mirrors or prisms (not shown) may be inserted into the observation optical path 9' to divert the beams in path 9' through the optical filter 17.

Light arriving at the image sensor 11 is converted into a two-dimensional image, which is then analyzed by the processor 104 of FIG. 1, as described above. In one example embodiment herein, differences in intensities of the fluorescence light detected from the dental enamel can be indicative of dental caries, and can enable detection and diagnosis of dental caries. As described above, areas of dental enamel having reduced fluorescence intensity can indicate the presence of dental caries.

Notably, the same optical source 3 and image sensor 11 useful for both 3-D imaging by parallel confocal imaging and caries detection by quantitative light-induced fluorescence, are included within the same camera 400. Referring to FIG. 1 in conjunction with FIG. 4, camera 400 can provide data to the processor 104 to create both a 3-D imaging data set and a caries detection data set, which can then be readily combined by the mapping device 106 and displayed as a diagnostic rendering on display 108, as described above.

Also notable is that the confocal optics 408a of the 3-D imaging mode, having a variable focal length, and the long depth of field optics 408b of the caries detection mode, having a fixed focal length, are both usable in the same camera 400.

In view of the foregoing description of the present embodiment, it can be appreciated that both the 3-D imaging mode and caries detection mode can be carried out using the same single camera 400, and the 3-D imaging data set and the caries detection data set can be readily combined by mapping device 106.

Figure 5:
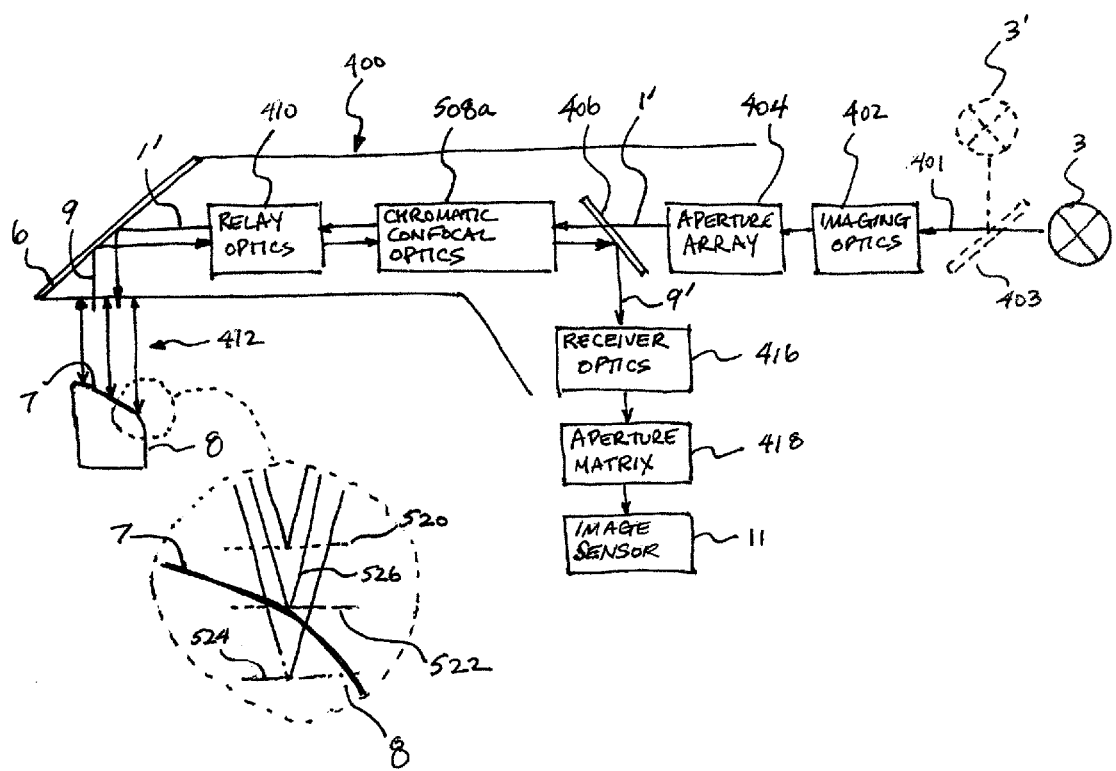
FIG. 5 is a block diagram of the camera of FIG. 4 wherein the interchangeable optic includes chromatic confocal optics and the camera performs chromatic confocal imaging while operating in the imaging mode.

Another example embodiment will now be now described. This example embodiment is similar to the embodiment described above and illustrated in FIG. 4 except that, in the present embodiment, the 3-D imaging mode is provided by means of chromatic confocal imaging as illustrated in FIG. 5. Particularly, the present embodiment may use the same components as the embodiment described above and illustrated in FIG. 4 except that the interchangeable optics 408 enabling the 3-D imaging mode may be, for example, chromatic confocal optics 508a of FIG. 5. The caries detection mode of the present example embodiment is provided by means of a quantitative light-induced fluorescence technique as described above in the embodiment illustrated in FIG. 4b.

Referring to FIG. 4, an optical source 3 produces a beam 401. Preferably, the optical source 3 emits polychromatic white light. Light propagates projection optical path 1' by way of devices 402, 404, 406, 408, 410, and 6 as described above. Light backscatters from the surface 7 of object 8 and propagates through the camera 400 by way of devices 6, 410, 408, 406, 416, and 418 to reach image sensor 11.

FIG. 5 illustrates an example case where the switch device 102 is set to 3-D imaging mode. As described above, in 3-D imaging mode, the interchangeable optics 408 of FIG. 4 may be chromatic confocal optics 508a of FIG. 5. The chromatic confocal optics 508a includes, for example, a diffractive optical element, a refractive optical element, or a combination of diffractive and refractive optical elements. The chromatic confocal optics 508a can impart axial chromatic dispersion on each beam of the array of light beams 412 passing through it to define a continuum of wavelength-encoded focal points, exemplified by λ1 focal point 520, λ2 focal point 522, and λ3 focal point 524, disposed along a Z-axis defined as part of the projection optical path 1' outside of camera 400.

Referring to the inset image of FIG. 5, during 3-D imaging mode, an example of the chromatic confocal principle for a single beam of the array of light beams 412 is presented herein. The surface 7 of object 8, which surface 7 may or may not be even, may be positioned within the continuum of wavelength-encoded focal points of the beam. Due to the chromatic dispersion imparted on the beam by chromatic confocal optics 508a, only one specific component wavelength λ2 526 of the beam is in focus on the surface 7 of object 8 at λ2 focal point 522.

Referring now to the full FIG. 5, as the beam backscatters and follows observation optical path 9 and 9' (by way of devices 6, 410, 508a, 406, and 416), the in-focus wavelength λ2 will be in focus at the aperture matrix 418 and pass through to a pixel sensor of the image sensor 11. Other wavelengths will be out of focus and attenuated by the aperture matrix 418, resulting in a lower intensity of those wavelengths at image sensor 11 than wavelength λ2. The pixel sensor of the image sensor 11 can be sensitive to a range of wavelengths, for example, the range of wavelengths emitted by the optical source 3, or in another example, a wavelength range corresponding to the continuum of wavelength-encoded focal points. The image sensor 11 provides a two-dimensional image, including, for example, a representation of the detected light intensity as a function of wavelength at each pixel, to the processor 104 of FIG. 1. Because wavelengths correlate to a position along the Z-axis, the processor 104 of FIG. 1 can determine the position of the surface 7 of object 8 within the beam by performing spectral analysis of the backscattered light received at the pixel sensor of the image sensor 11. The spectral analysis may include, for example, determining the wavelength component of the backscattered light having the highest relative intensity, although this example is not limiting. The same principle can be applied over the entire array of light beams 412, each beam corresponding to a pixel sensor of the image sensor 11, to enable processor 104 of FIG. 1 to obtain a height image, the height image storing the position of surface 7 of object 8 along the Z-axis at each corresponding pixel. A 3-D imaging data set can be created from at one or more height image.

Caries detection mode and the method of obtaining a caries detection data set are similar to an embodiment described above and illustrated in FIG. 4b. The caries detection data set can be overlaid on the 3-D imaging data set to form a combined data set by mapping device 106 of FIG. 1. The 3-D imaging data set with caries detection data set overlaid can be presented to the user as a diagnostic rendering by display 108 of FIG. 1, as described above.

Notably, the same optical source 3 and image sensor 11 useful for both 3-D imaging by chromatic confocal imaging and caries detection by quantitative light-induced fluorescence can be combined in the same camera system.

Also notable is that the chromatic confocal optics 508a of the 3-D imaging mode, which generates focused chromatic dispersion, and the long depth of field optics 408b of the caries detection mode, having a fixed focal length and little to no dispersion, are both interchangeably combined in the same camera system.

In view of the foregoing description of the present embodiment, it can be appreciated that both the 3-D imaging mode and caries detection mode can be carried out using the same single camera 400, and the 3-D imaging data set and the caries detection data set can be readily combined by mapping device 106.

In one example embodiment herein, at least some components of the system shown in FIG. 1 (such as all those components besides camera 100 and object 8) can form or be included in a computer system. The computer system includes at least one computer processor (e.g. a central processing unit or a multiple processing unit), which may include at least one or more of the devices 102-106 (or one or more of those devices can be separate from the computer processor). The computer processor is connected to a communication infrastructure (e.g., a communications bus, a cross-over bar device, or a network) (not shown).

The computer system also can be connected to the camera 100, including any one of the components therein, such that the computer system can perform capturing of images while the camera 100 operates in the imaging mode and/or diagnostic mode.

The computer system also includes an output user interface, such as display 108 or any other suitable type of device that outputs user-perceptible information.

The computer system also can include an input user interface that can be used by a user of the computer system to send information to the computer processor. For example, the input unit can include a keyboard device, a display user-interface, switch device 102, and/or a mouse device or other input device. In one example, the display 108 and the input user interface can collectively form a user interface.

In addition, the computer system includes one or more memories (not shown), such as a random access memory ("RAM"), a hard disk drive, and/or a removable-storage drive (e.g., a floppy disk drive, a magnetic tape drive, an optical disk drive, a flash memory drive, and the like). The removable-storage drive reads from and/or writes to a removable storage unit in a well-known manner. The removable storage unit may be, for example, a floppy disk, a magnetic tape, an optical disk, a flash memory device, and the like, which is written to and read from by the removable-storage drive. The memories can include a non-transitory computer-readable storage medium storing computer-executable software instructions and/or data.

One or more computer programs are stored in the memories. The computer programs include computer-executable instructions which, when executed by the computer processor, cause the computer system to perform the procedures of switch device 102, processor 104, and mapping device 106, and procedures for capturing images in an imaging mode and a diagnostic mode of camera 100, for example, and/or any procedures described herein.

What is claimed is:

1. A dental imaging system, comprising:
 a housing;
 an optical system that includes:
  at least one optical source,
  an imaging sensor,
  a prism configured to deviate a light beam emitted by the at least one optical source onto an object and deviate light backscattered by the object onto the imaging sensor, wherein a path of the light beam, from the optical source to the object, defines a projection optical path and a path of the light backscattered by the object, from the object to the imaging sensor, defines an observation optical path, and
  a grating configured to move between a first position, where the grating is in the projection optical path, and a second position, where the grating is not in the projection optical path,
  wherein the at least one optical source and the imaging sensor are contained within the housing, and
  wherein the optical system is configured to produce three-dimensional image data of an object using the imaging sensor while the optical system operates in an imaging mode, and is further configured to produce caries detection data of the object using the imaging sensor while the optical system operates in a diagnostic mode; and
 at least one processing system arranged to combine the three-dimensional image data and the caries detection data into a diagnostic rendering,
 wherein the grating is disposed at the first position in the imaging mode and at the second position in the diagnostic mode.

2. A system according to claim 1, wherein the optical system operates in the imaging mode and the diagnostic mode non-simultaneously.

3. A system according to claim 1, wherein the optical system is operable to select at least one of the imaging mode and the diagnostic mode.

4. A system according to claim 1, wherein an integration time of the imaging sensor during the diagnostic mode is increased relative to the imaging mode.

5. A system according to claim 1,
 wherein the optical system performs three-dimensional imaging by phase-shift triangulation while operating in the imaging mode, and performs transillumination imaging while operating in the diagnostic mode.

6. A system according to claim 1, wherein the optical system is a self-contained camera.

7. A method for operating a dental imaging system, the method comprising:
 producing in an imaging mode of the dental imaging system three-dimensional image data of an object using an imaging sensor;
 producing in a diagnostic mode of the dental imaging system caries detection data of the object using the imaging sensor; and
 combining the three-dimensional image data and the caries detection data into a diagnostic rendering,
 wherein the dental imaging system comprises an optical system that comprises:
  at least one optical source,
  the imaging sensor,
  a prism configured to deviate a light beam emitted by the at least one optical source onto the object and deviate light backscattered by the object onto the imaging sensor, wherein a path of the light beam, from the optical source to the object, defines a projection optical path and a path of the light backscattered by the object, from the object to the imaging sensor, defines an observation optical path, and
  a grating configured to move between a first position, where the grating is in the projection optical path, and a second position, where the grating is not in the projection optical path, and
 wherein the grating is disposed at the first position in the imaging mode and at the second position in the diagnostic mode.

8. A method according to claim 7, wherein the producing in the imaging mode and the producing in the diagnostic mode occur non-simultaneously.

9. A method according to claim 7, wherein the producings are selectable.

10. A method according to claim 7, wherein the producing in the imaging mode includes performing three-dimensional imaging by phase-shift triangulation, and the producing in the diagnostic mode includes performing transillumination imaging.

11. A method according to claim 7, wherein the dental imaging system is a self-contained camera.

12. A method according to claim 7, wherein an integration time of the imaging sensor during the diagnostic mode is increased relative to the imaging mode.

13. A non-transitory computer-readable medium having instructions stored thereon which, when executed, cause a dental imaging system, that comprises an optical system that comprises:
 at least one optical source,
 an imaging sensor,
 a prism configured to deviate a light beam emitted by the at least one optical source onto an object and deviate light backscattered by the object onto the imaging sensor, wherein a path of the light beam, from the optical source to the object, defines a projection optical path and a path of the light backscattered by the object, from the object to the imaging sensor, defines an observation optical path, and
 a grating configured to move between a first position, where the grating is in the projection optical path, and a second position, where the grating is not in the projection optical path, to perform a procedure comprising:
producing in an imaging mode of the dental imaging system three-dimensional image data of an object using the imaging sensor,
producing in a diagnostic mode of the dental imaging system caries detection data of the object using the imaging sensor, and
combining the three-dimensional image data and the caries detection data into a diagnostic rendering,
wherein the grating is disposed at the first position in the imaging mode and at the second position in the diagnostic mode.

14. The program according to claim 13, wherein the combining includes mapping the caries detection data onto the three-dimensional image data.

* * * * *